US008167833B2

(12) United States Patent  
Tashiro

(10) Patent No.: US 8,167,833 B2
(45) Date of Patent: May 1, 2012

(54) BREAST PUMP

(75) Inventor: Mitsuo Tashiro, Tokyo (JP)

(73) Assignee: Pigeon Corporation, Tokyo (JP)

( * ) Notice: Subject to any disclaimer, the term of this patent is extended or adjusted under 35 U.S.C. 154(b) by 54 days.

(21) Appl. No.: 12/827,429

(22) Filed: Jun. 30, 2010

(65) Prior Publication Data

US 2011/0004155 A1 Jan. 6, 2011

(51) Int. Cl.
*A61M 1/06* (2006.01)
(52) U.S. Cl. ........................................................ 604/74
(58) Field of Classification Search .................. 604/74, 604/119, 29; 471/44.9, 477.2
See application file for complete search history.

(56) References Cited

U.S. PATENT DOCUMENTS

| 4,886,494 | A | * | 12/1989 | Morifuji | 604/74 |
| 5,542,921 | A | * | 8/1996 | Meyers et al. | 604/74 |
| 6,299,594 | B1 | * | 10/2001 | Silver | 604/74 |
| 6,840,918 | B1 | * | 1/2005 | Britto et al. | 604/74 |
| 7,413,557 | B2 | * | 8/2008 | Samson et al. | 604/74 |
| 7,641,629 | B2 | * | 1/2010 | Yuen | 604/74 |
| 2002/0032404 | A1 | * | 3/2002 | Silver | 604/74 |
| 2008/0275386 | A1 | * | 11/2008 | Myers | 604/74 |

FOREIGN PATENT DOCUMENTS

JP 2006-102220 A 4/2006

* cited by examiner

*Primary Examiner* — Jackie Ho
*Assistant Examiner* — Diva K Chander
(74) *Attorney, Agent, or Firm* — Kenealy Vaidya LLP

(57) ABSTRACT

The present disclosed subject matter provides a breast pump in which, by the use of an operation performed by a user, the negative pressure (suctioning pressure) can be adjusted in accordance with the amount of the operation in a linear fashion without the occurrence of a steep gradient, and the negative pressure can be readily adjusted even during the expression of milk.

9 Claims, 10 Drawing Sheets

BREAST PUMP

This application claims the priority benefit under 35 U.S.C. §119 of Japanese Patent Application No. 2009-15688 filed on Jul. 1, 2009, which is hereby incorporated in its entirety by reference.

FIELD

The present disclosed subject matter relates to an improvement in a breast pump for expressing milk.

DESCRIPTION OF THE RELATED ART

A conventionally used breast pump comprises, for example, a horn section for abutting against a breast, and negative pressure generating means or structure, such as a pump, for creating a negative pressure in a space formed by abutting the horn section against the breast. Breast milk suctioned into the negative pressure space is collected by dropping down into a bottle or the like, and the negative pressure forming space and the pump are connected by means of a channel (see Japanese Patent Application Laid-open No. 2006-102220).

A breast pump having a structure of this kind has a pressure transmitting section which transmits pressure when expressing milk and a ventilation channel is connected to the case of this pressure transmitting section. Pressure adjustment means or structure is provided at an intermediate point of the ventilation channel; the pressure adjustment means or structure is provided directly at intermediate point in the ventilation channel and the leakage volume of air exiting to the exterior from an opening which is connected to the exterior and which is formed at an intermediate point of the ventilation channel can be adjusted by altering the diameter of the opening (opening surface area) through rotating and adjusting a knob (dial) of the pressure adjustment means or structure. By this means, a user is able to adjust the negative pressure inside the negative pressure forming space which is created by abutting the horn section against a breast.

SUMMARY OF THE DISCLOSED SUBJECT MATTER

FIG. 10 shows the relationship between the angle of rotation of the dial and the suctioning pressure (negative pressure) in a prior art breast pump of this kind; when the user rotates the dial and increases the angle of rotation of the dial, the suctioning pressure increases with a steep gradient and tends to rise suddenly as shown in FIG. 10. On the contrary, when the user turns the dial in the opposite direction and decreases the angle of rotation of the dial, the suctioning pressure tends to decrease suddenly.

Therefore, since the air leakage volume is essentially a very small volume, even if the user increases the angle of rotation of the dial little by little, when adjusting the air leakage volume, the suctioning pressure still increases suddenly and therefore it is difficult to adjust the air leakage volume during expression of milk, it is difficult to adjust the negative pressure inside the negative pressure forming space, and the reproducibility of the negative pressure adjustment operation is poor.

Therefore, according to an aspect of the presently disclosed subject matter one can provide a breast pump in which, by means of an operation performed by a user, the negative pressure (suctioning pressure) can be adjusted in accordance with the amount of the operation in a linear fashion without the occurrence of a steep gradient, and the negative pressure can be readily adjusted even during the expression of milk.

According to the another aspect of the disclosed subject matter, a breast pump can be provided having a substantially conical milk expressing section which abuts against a user's breast, and a breast pump main body which includes the milk expressing section and is attachable to and detachable from a bottle so as to communicate with the bottle, the breast pump including pressure changing means or structure, connected to the milk expressing section, for alternately generating a negative pressure state and at least an atmospheric pressure state as a pressure higher than the negative pressure state; a deformable member, which is provided so as to liquid-tightly separate a sealed space formed by abutment of the milk expressing section against the user's breast or a space connected to the sealed space, from the pressure changing means or structure, and which is capable of deforming in order to adjust the negative pressure state of the milk expressing section by transmission of the pressure that is changed by the pressure changing means or structure; and pressure adjustment means or structure for adjusting the negative pressure by changing the amount of deformation of the deformable member.

In contrast to a structure in which fine adjustment is difficult in practice, for instance, a structure which adjusts the diameter of a leakage hole which is a very small opening, as in a conventional pressure adjustment means or structure, the actual amount of negative pressure created is adjusted by changing the amount of deformation of the deformable member, and therefore it is possible to adjust, by means of an operation performed by the user, the negative pressure (suctioning pressure) in accordance with the amount of operation in a linear fashion without a steep gradient, and it is possible to readily adjust the negative pressure even during the expression of milk.

In the disclosed subject matter, the pressure adjustment means or structure can include a base section; an adjustment dial which is provided on the base section and can be rotated by the user; and a stopper which is provided inside the deformable member, and adjusts the amount of deformation of the deformable member by moving with respect to the base section due to the rotation of the adjustment dial.

Thus, simply by rotating the adjustment dial, the user is able to cause the stopper to project inside the deformable member and thereby adjust the negative pressure (suctioning pressure) in accordance with the amount of projection of the stopper in a linear fashion without the occurrence of a steep gradient. As a result, the negative pressure can be readily adjusted even during the expression of milk.

According to another aspect of the disclosed subject matter, the pressure adjustment means or structure can include a base section having a wall portion which upstands inside the deformable member; an adjustment dial which is provided on the base section and can be rotated by the user; and a partial tubular section which is provided inside the deformable member, and adjusts the amount of deformation of the deformable member by projecting inside the deformable member from the wall portion by rotating from a state of overlapping with the wall portion of the base section, due to the rotation of the adjustment dial.

Thus, simply by means of the user turning the adjustment dial, the partial tubular section is made to project inside the deformable member from the wall portion, and the user is able to adjust the negative pressure (suctioning pressure) in accordance with the amount of rotation of the partial tubular section in a linear fashion without the occurrence of a steep gradient. As a result, the negative pressure can be readily adjusted even during the expression of milk.

As described previously, according to an aspect of the present disclosed subject matter, it is possible to provide a breast pump in which, by means of an operation performed by a user, the negative pressure (suctioning pressure) can be adjusted in accordance with the amount of the operation in a linear fashion without the occurrence of a steep gradient, and the negative pressure can be readily adjusted even during the expression of milk.

DESCRIPTION OF EXEMPLARY EMBODIMENTS

Below, an embodiment of the present disclosed subject matter is described in detail on the basis of the accompanying drawings.

The embodiments described below are concrete examples of the presently disclosed subject matter and therefore are subject to various desirable technical restrictions, but the scope of the presently disclosed subject matter is not limited to these modes.

Figure 1:
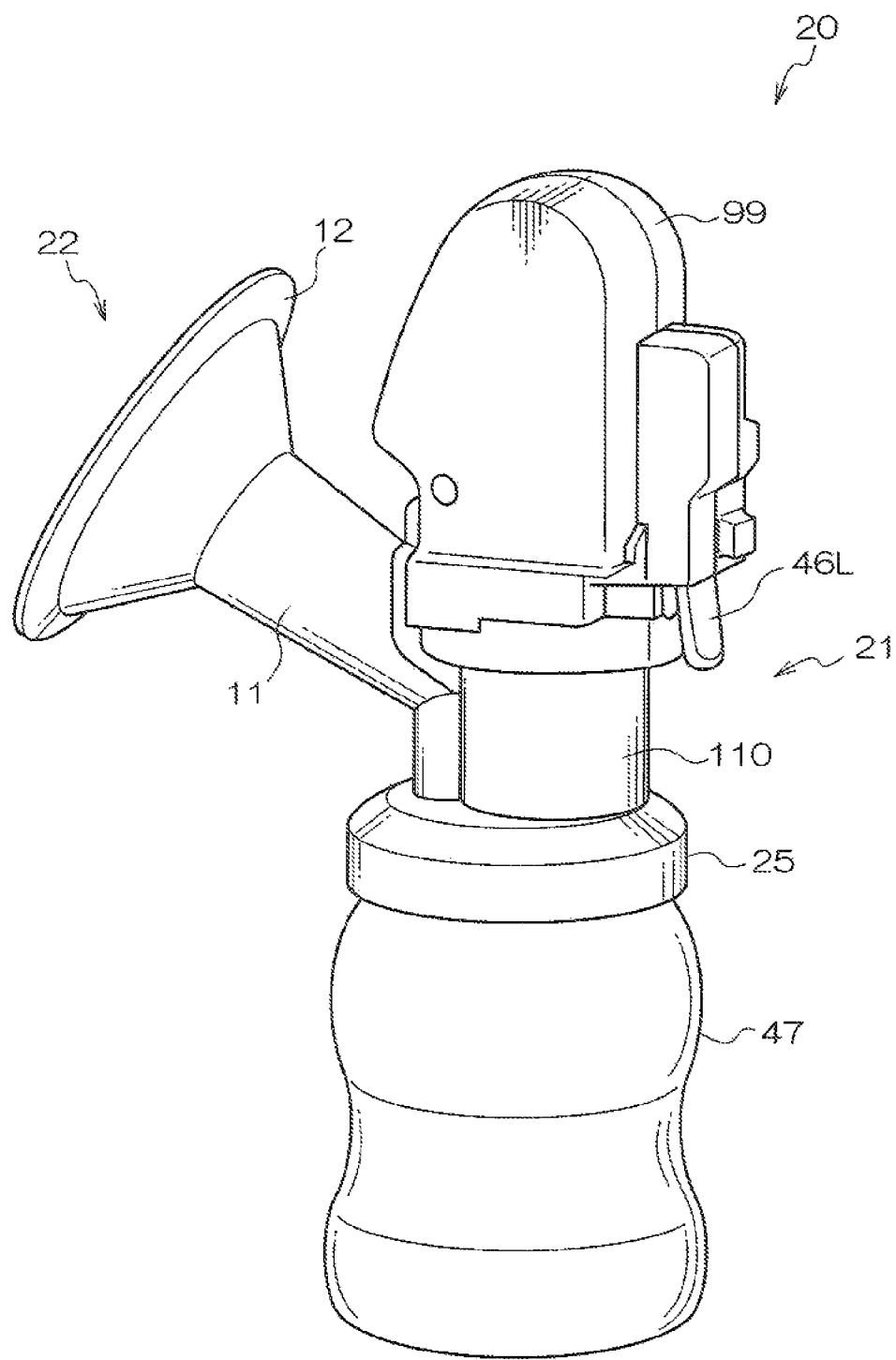
FIG. 1 is a perspective diagram showing the composition of a breast pump relating to an embodiment of the presently disclosed subject matter.
Figure 2:
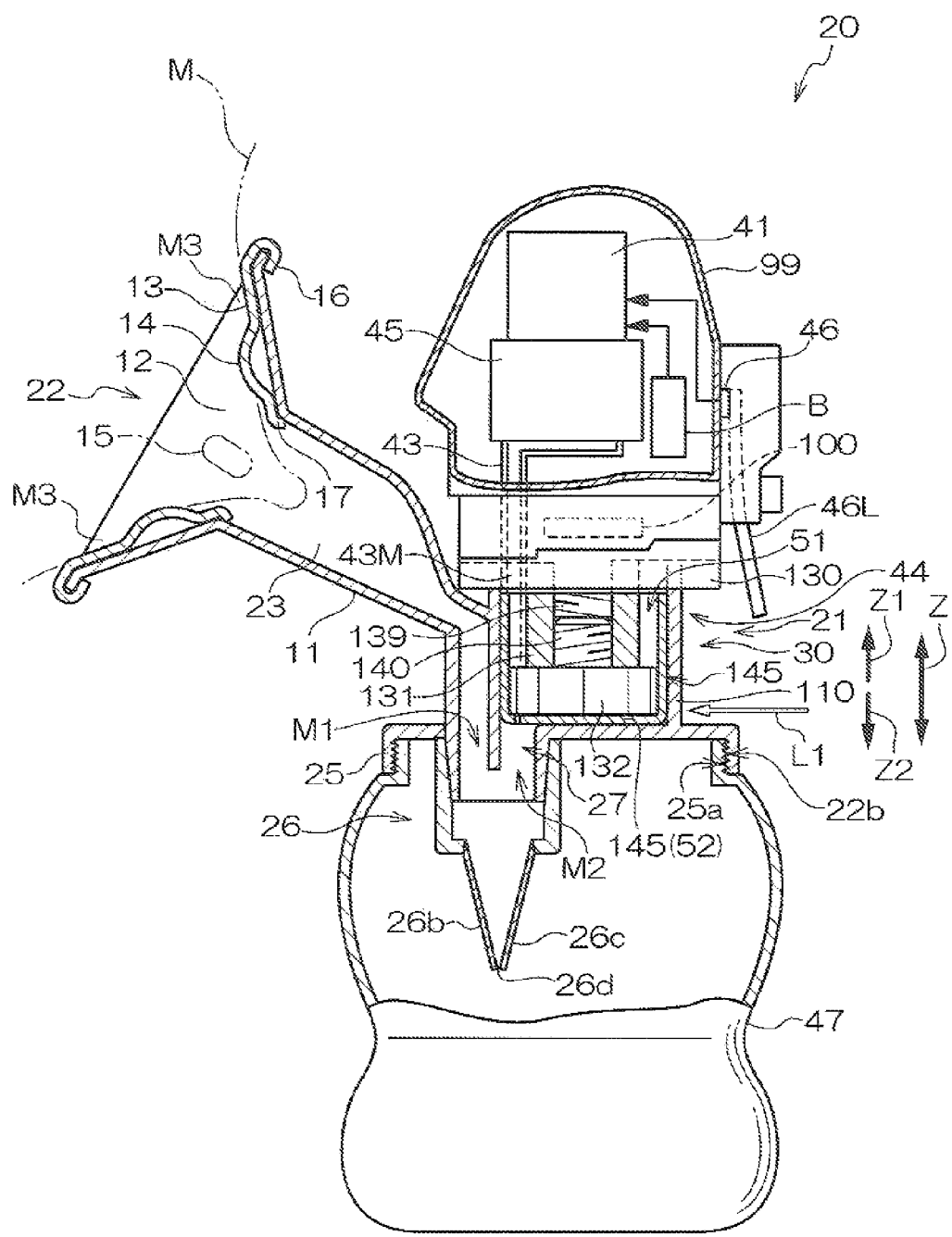
FIG. 2 is a side view diagram including a partial cross-section showing a breast pump.
Figure 3:
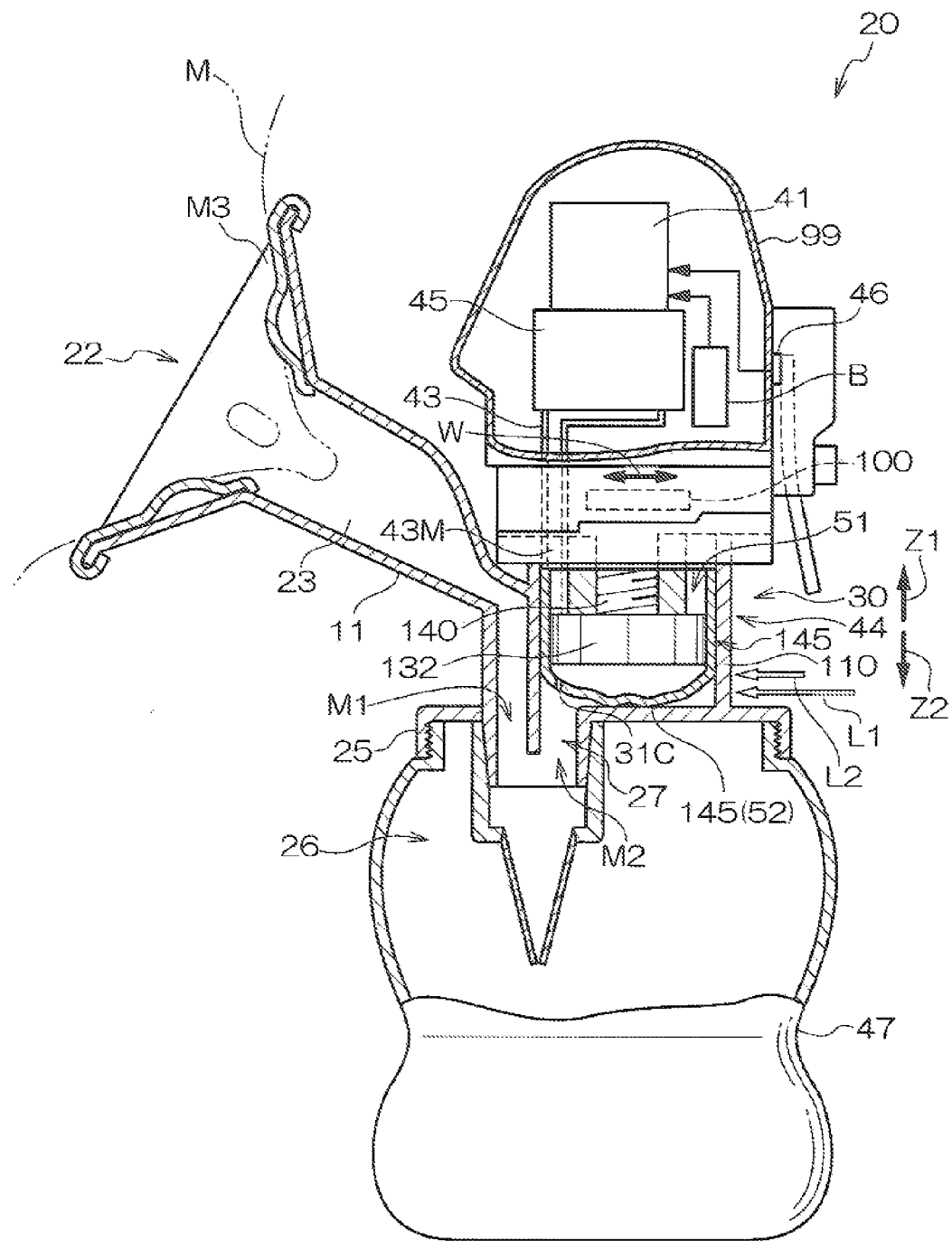
FIG. 3 is a side view diagram including a partial cross-section showing a breast pump.

FIG. 1 is a perspective diagram showing the composition of a breast pump relating to an embodiment of the presently disclosed subject matter. FIG. 2 and FIG. 3 are side view diagrams of the breast pump including a partial cross-sectional view.

FIG. 1 to FIG. 3 show a general view of a breast pump 20. As shown in FIG. 1, the breast pump 20 can include a bottle 47, which is a container for collecting breast milk that has been expressed, and a breast pump main body 21 (hereinafter, called "the main body") which can be attached to and detached from the bottle 47.

The main body 21 shown in FIG. 1 is made entirely of a relatively soft and pliable material, such as a synthetic resin material, for example, polycarbonate, polycycloolefin, polyether sulfone, polyamide, polypropylene, or the like. The main body 21 can include an attachment section 25 which attaches to the bottle 47 in order to collect breast milk that has been expressed, a case 110, and a milk expressing section 22. As shown in FIG. 2, for example, the attachment section 25 is a flat cylindrical portion which comprises a female screw section 25a on the inner side thereof, and screws together with a male screw section 22b formed on the outer perimeter of the neck of the bottle 47. The bottle 47 may be a special part for the breast pump 20 or it may employ a generic feeding bottle which is suited to the attachment section 25.

As shown in FIG. 2, a conical or horn-shaped milk expressing section 22 which is open to the outside is provided in an obliquely inclined state on the upper portion of the attachment section 25 of the main body 21. The milk expressing section 22 comprises an open channel 11 which gradually broadens and constitutes a ventilation channel 23, and provided in an integrated fashion on the front end side of the open channel 11, an open front end section 12 which expands broadly in a horn shape. These elements are made of the same material as the main body 21 and have relatively high rigidity and are not readily deformable.

Furthermore, a tubular deformable member 13 having substantially the same shape as the open front end section 12 is provided on the inner side of the open front end section 12 shown in FIG. 2. The deformable member 13 is attached to the inner side of the open front end section 12, by means of an engaging section 17 on the base end side and a front end engaging section 16 which covers and surrounds the edge portion of the opening M3. This deformable member 12 is made of an elastic body, such as silicone rubber, elastomer, natural rubber, or the like.

As shown in FIG. 2, convex-shaped stimulating sections 14 which project inwards in the upward and downward directions are formed at two positions in the circumferential direction of the deformable member 13, and deformation guide sections 15 are formed at two positions in the circumferential direction where the convex-shaped stimulating sections 14 are not provided.

The convex-shape stimulating sections 14 shown in FIG. 2 abut and press against the breast when the negative pressure in the sealed space is high, thereby imparting a desirable stimulus to accompany the expression of milk, and displaying a massaging effect. The deformation guide sections 15 are formed with a thin material thickness at the corresponding locations, so as to have lower rigidity and be more readily deformable than the other regions.

As shown in FIG. 2, the ventilation channel 23 of the milk expressing section 22 forms a channel for the passage of air and expressed breast milk, and has a tubular shape which gradually expands in the oblique upward direction; the narrow end portion of the ventilation channel 23 of the milk expressing section bends vertically downwards and faces toward the bottle 47. The opening M1 of the ventilation channel 23 of the milk expressing section 22 connects with the inner side of the attachment section 25 of the main body 21 and the bottle 47, and a small chamber 26 forming a small space is formed in the vicinity of the opening M1. This small chamber 26 projects downwards inside the bottle 47.

A further ventilation channel 27 is provided adjacently to the ventilation channel 23 of the milk expressing section. Moreover, the lower end opening M2 of the ventilation channel 27 connects with the ventilation channel 23 of the milk expressing section via the small chamber 26, as shown in FIG. 2, and the upper end of the ventilation channel 27 extends upwards and connects with the case 110 of the pressure transmitting section 30.

As shown in FIG. 2, the small chamber 26 has a cup shape and is formed by an elastic body such as silicone rubber, elastomer, natural rubber, or the like, and the respective side walls 26b, 26c of the small chamber 26 are inclined walls of the elastic body formed so that the width therebetween gradually reduces toward the lower end, each of the side walls forming a valve body which is capable of minute movement. A slit 26d is provided in the mutually adjacent lower ends of the side walls 26b, 26c, and when expressed breast milk has collected to a prescribed volume in the small chamber 26a, the slit 26d in the front end side of the side walls 26b, 26c opens due to the change in pressure when the negative pressure is released, as described below, and due to the weight of the milk itself, in such a manner that the breast milk drops down inside the bottle 47.

Furthermore, by forming a slit 26d in the lower end of the inclined walls, the side walls are also able to function as an air valve which prevents the air inside the bottle 47 from entering into the small chamber 26 during the application of negative pressure.

As shown in FIG. 2, drive means or drive structure, for example, a motor 41, negative pressure creating means (or negative pressure creating structure) for creating a negative pressure which is driven by the motor, for example, a diaphragm 45, and a head section 99 which accommodates a battery B forming a power supply for driving the motor 41 are disposed on the case 110.

An air intake and exhaust tube extending from the diaphragm 45 constitutes a ventilation channel 43 and the lower end section 43M of the ventilation channel 43 is connected so as to communicate with the interior of the deformable member 145 inside the case 110 of the pressure transmitting section 30. By interposing a deformable member 145 inside the case 110 of the pressure transmitting section 30, the ventilation channel 27 of the case 110 and the ventilation channel 23 of the milk expressing section assume a hermetically sealed state from the diaphragm 45 and the ventilation channel 43 which constitute the pressure changing means or structure.

A switch 46 is connected to the motor 41 which drives the diaphragm 45. The switch 46 is provided on a switch lever 46L and the user is able to turn the switch 46 on and off by operating the switch level 46L.

By this means, the user is able to turn the switch on and off as she pleases and is able to generate a pulsating action at a desired timing.

Of course, it is also possible to provided a drive control section which incorporates prescribed circuitry, in which case a merit is obtained in that the user is able to obtain a predetermined pulsating action without herself determining the on and off driving of the motor.

However, if a drive control section is not provided, then it is possible to reduce the manufacturing costs accordingly.

By this means, when the switch 46 shown in FIG. 2 is turned on and the motor 41 and the diaphragm 45 are driven, the connected space, in other words, the negative pressure forming space which is created by the internal space of the case 110, the ventilation channel 23 of the milk expressing section 22, the ventilation channel 27 and the small chamber 26 can be set to a negative pressure (suctioning pressure).

In this case, if the drive control section described above is provided, it is possible to create pulsating states by switching on and off at prescribed time intervals on the basis of the control modes of this section. Alternatively, it is also possible to create a pulsation action in accordance with the timing of switching performed by the user, as in the present embodiment. In either case, it is desirable to perform pressure variations which create a pulsating action whereby the pressure changes and continues to change from a negative pressure to at least an atmospheric pressure state.

The case 110 of the pressure transmitting section 30 shown in FIG. 2 is a tubular body which is long in the vertical direction, for example, and the deformable member 145 is accommodated inside this case 110. The case 110 is formed between the head section 99 and the attachment section 25. The deformable member 145 disposed inside this case 110 is, for example, a bottomed cylindrical body having an opening 51 at one end thereof and the other end thereof forming a closed bottom section 52; the deformable member 145 is formed by a molded article made of synthetic rubber, such as silicone, having a certain degree of flexibility.

The opening 51 of the deformable member 145 is open on the upper side and the outer perimeter of the deformable member 145 makes tight contact with the inner circumferential surface of the case 110.

By this means, in the main body 21, when a breast is abutted against the milk expressing section 22 and the opening M3 thereof is closed off, the portion to the inner side thereof, namely, the ventilation channel 23 of the milk expressing section 22, the small chamber 26, the ventilation channel 27, and the bottom section 52 of the deformable member 145 in the case 110 create a hermetically sealed space. By sealing the outer perimeter of the opening 51 of the deformable member 145 against the inner circumferential surface of the case 110, the aforementioned hermetically sealed space, the motor 41 and the diaphragm 45 are sealed in a completely airtight and liquid-tight fashion, so that no air or liquid can leak from same.

As shown in FIG. 2, pressure adjustment means or structure 44 is disposed inside the case 110.

This pressure adjustment means or structure 44 has an adjustment dial 100 in such a manner that the user, for example, can change and finely adjust the negative pressure (suctioning pressure) inside the ventilation channel 23 of the milk expressing section, the ventilation channel 27 and the case 110, by rotating and adjusting this adjustment dial 100 as she desires.

Next, this pressure adjustment means or structure 44 will be described with reference to FIG. 2 to FIG. 7.

Figure 4:
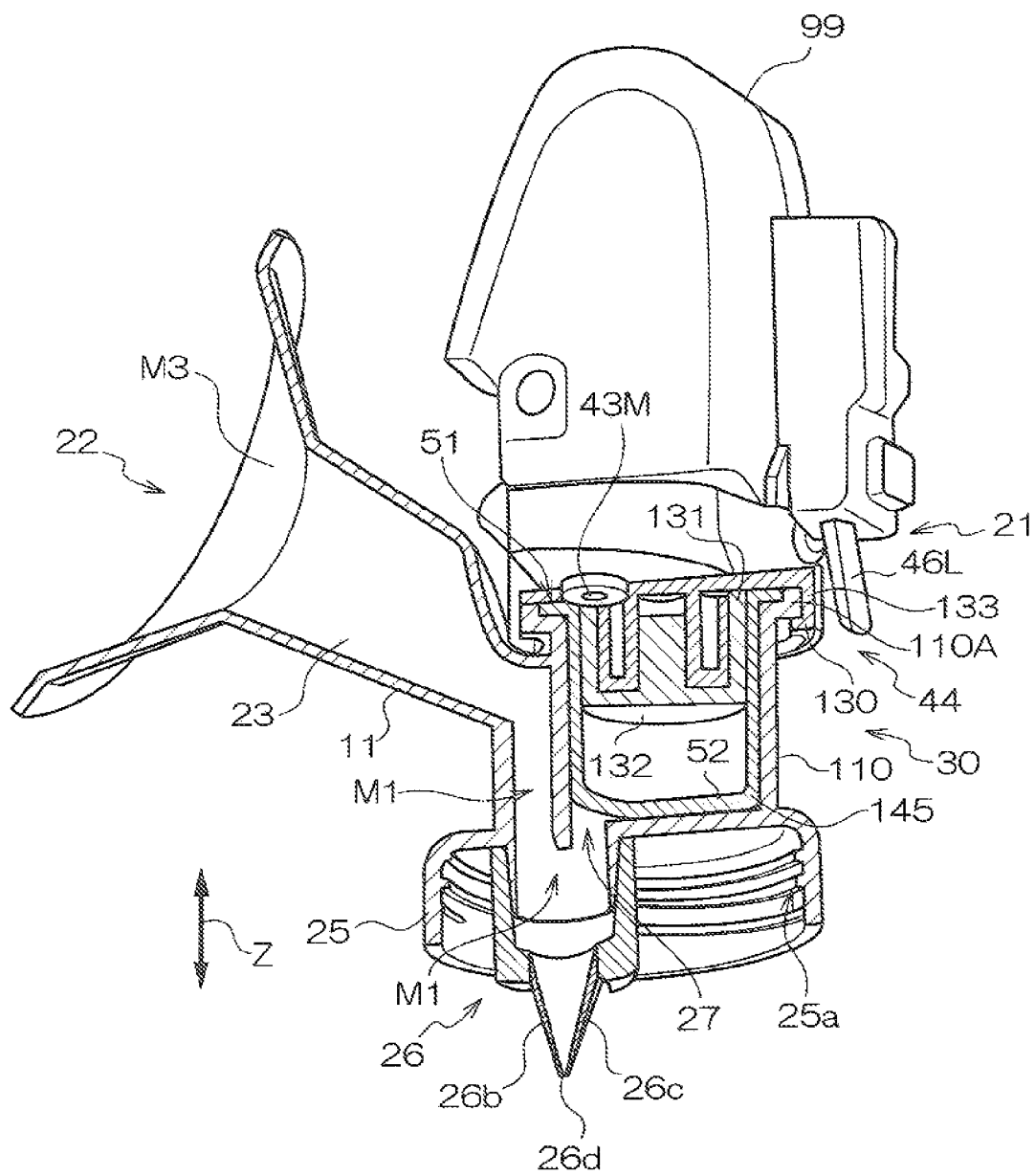
FIG. 4 is a perspective diagram including a partial cross-section showing the vicinity of an elongated section, pressure adjustment means or structure, an attachment section and a head section.
Figure 5:
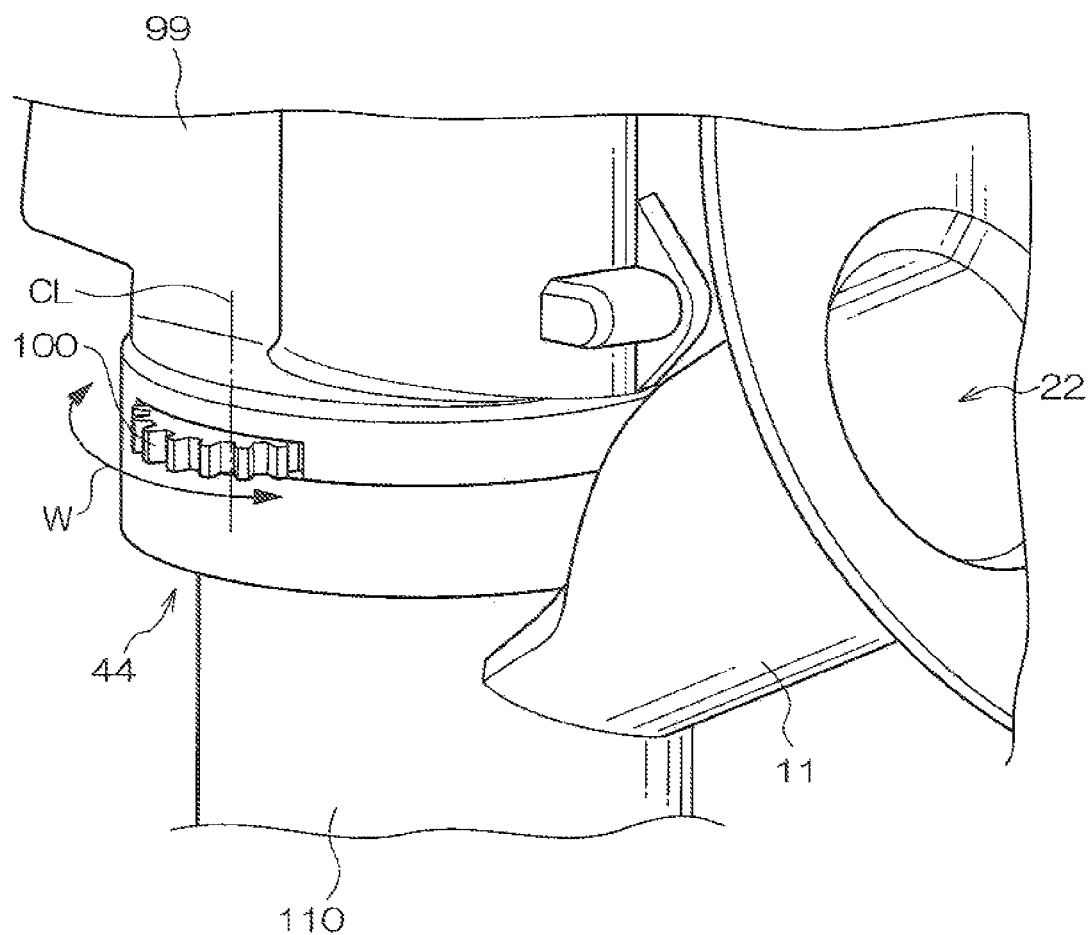
FIG. 5 is a perspective diagram showing the vicinity of the adjustment dial of pressure adjustment means or structure.
Figure 6:
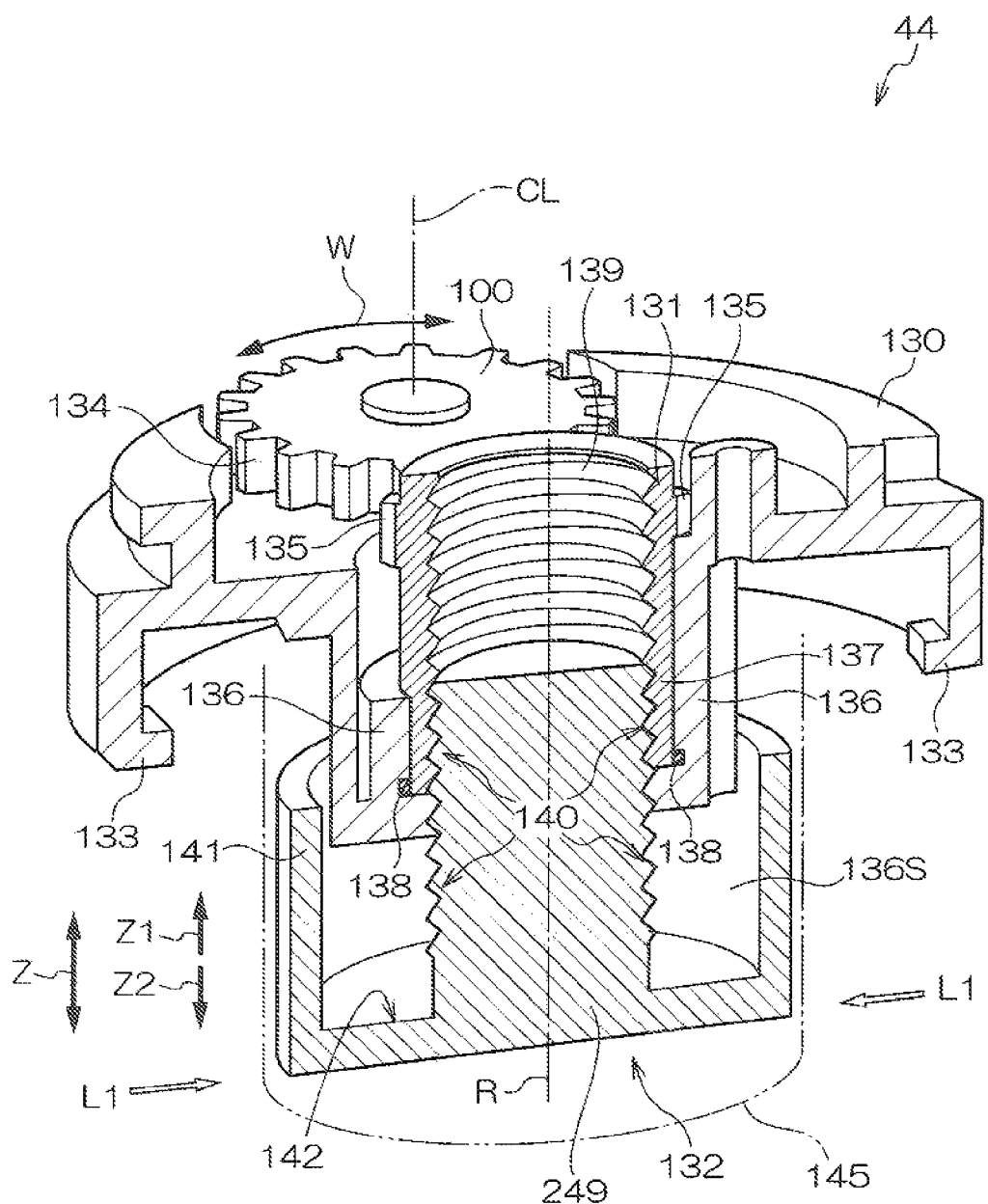
FIG. 6 is a perspective diagram corresponding to FIG. 2, showing a state before the operation of the pressure adjustment means or structure.

FIG. 2 and FIG. 3 show variation in the operation of the pressure adjustment means or structure 44, and FIG. 4 is a perspective diagram including a partial cross-section showing the vicinity of the case 110, the pressure adjustment means or structure 44, the attachment section 25 and the head section 99. FIG. 5 is a perspective diagram showing the vicinity of the adjustment dial 100 of the pressure adjustment means or structure 44. FIG. 6 is a perspective diagram corresponding to FIG. 2 which shows a state before operation of the pressure adjustment means or structure 44, and FIG. 7 is a perspective diagram corresponding to FIG. 3 which shows a state after operation of the pressure adjustment means or structure 44.

The case 110 shown in FIG. 2 is formed so as to project upwards on the upper side of the attachment section 25, and the case 110 is substantially a tubular portion. The ventilation channel 27 is connected to the inner space of the bottom section 52 side of the deformable member 145 in the case 110.

Figure 7:
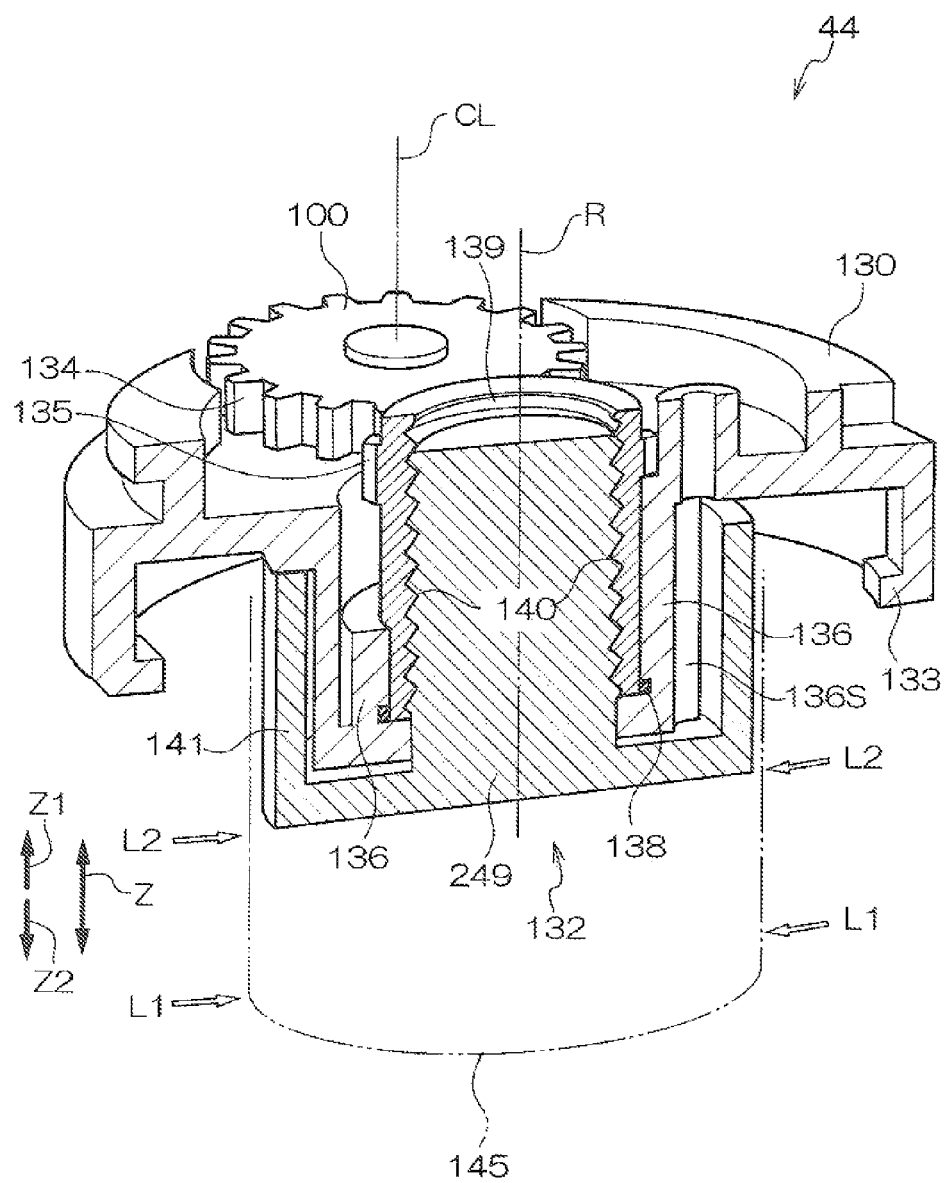
FIG. 7 is a perspective diagram corresponding to FIG. 3, showing a state before the operation of the pressure adjustment means or structure.

The structure of the pressure adjustment means or structure 44 is described now with reference to FIG. 6 and FIG. 7. The pressure adjustment means or structure 44 makes it possible to achieve fine pressure adjustment by adjusting the volume of the deformable member 145 used to prevent reflux inside the ventilation channel 27, and adjusting the negative pressure state of the milk expressing section 22, in other words, by changing, in a linear fashion without the occurrence of a steep gradient, the negative pressure (breast milk suctioning pressure) inside negative pressure forming space which is created by abutting the horn section against the breast (namely, the internal space of the ventilation channel 23 of the milk expressing section, the ventilation channel 27 and the case 110).

Firstly, the deformable member 145 shown in FIG. 2 and FIG. 4 will be described. As stated previously, this deformable member 145 is made of a material having flexibility and shape restoring properties, such as silicone, and as shown in FIG. 4, the deformable member 145 has a substantially U-shaped cross-section, in which the upper portion 51 is open and the lower portion thereof is closed and forms the bottom section 52, the deformable member 145 being disposed inside the case 110. A flange portion of the upper section 51 of the deformable member 145 is interposed, sandwiched and fixed between the upper end portion 111A of the case 110 and the inner surface of an attachment section 133 of a base section 130.

As shown in FIG. 6 and FIG. 7, the pressure adjustment means or structure 44 comprises a substantially circular base section 130, a rotating member 131, a stopper member 132 and an adjustment dial 100. In FIG. 6 and FIG. 7, the base section 130, the rotating member 131 and the stopper member 132 are shown in vertical cross-section in order to depict their internal shapes. The case section 130 has an attachment section 133 arranged about the whole circumferential direction thereof. As stated previously, the upper end portion 110A of the case 110 is fixed in a sealed fashion by fitting the attachment section 133 shown in FIG. 4 into the upper end portion 110A of the case 110.

As shown in FIG. 6, an adjustment dial 100 is installed rotatably about a central axis CL on the upper surface of the base section 130. A gear 134 is formed about the whole circumference of the outer perimeter of this adjustment dial 100. The base section 130 has a tubular case portion 136.

The rotating member 131 shown in FIG. 6 is a tubular member and a gear 135 is formed about the whole circumference thereof, in an upper position of the outer circumferential portion of the rotating member 131. This gear 135 meshes with the gear 134 on the outer circumference of the adjustment dial 100. The lower position 137 of the rotating member 131 is installed rotatably about an axis R inside the case portion 136 of the base section 130. An O-ring 138 is provided between the lower position 137 and the case portion 136 in order to create a hermetic seal. The central axis CL and the central axis R are parallel and lie in the vertical direction. A female screw portion 139 is formed in the inner circumferential portion of rotating member 131.

There are no particular restrictions on the material used for the stopper member 132 shown in FIG. 6, but good reproducibility of pressure adjustment is obtained if a hard member made of ABS, polycarbonate, polypropylene, or the like, is used.

The stopper member 132 has a columnar section 249, a male screw section 140, a cylindrical perimeter portion 141, and a bottom surface section 142. The male screw section 140 is formed from the upper end portion to the lower end portion of the outer circumferential surface of the columnar section 249. The male screw section 140 intermeshes with the female screw section 139. A space section 136S of a size into which the case portion 136 can be inserted is provided on the inner side of the perimeter portion 141.

In this way, by means of the user suitably rotating the adjustment dial 100 with her finger, the adjustment dial 100 is able to cause the rotating member 131 to rotate in the opposite direction to the rotation of the adjustment dial 100. Consequently, by rotating the rotating member 131, the position of the stopper member 132 can be raised in the Z1 direction as indicated by the state shown in FIG. 7, from the state shown in FIG. 6.

The stopper member 132 is positioned inside the deformable member 145 shown in FIG. 2 and FIG. 4, and the stopper member 132 is a substantially tubular stopper which maintains the position of the deformable member 145 in the vertical direction Z. More specifically, as shown in FIG. 2 and FIG. 6, when the stopper member 132 is positioned in the lowermost position L1, the outer shape of the deformable member 145 is maintained reliably up to the position of bottom section inside the case 110.

However, as shown in FIG. 3 and FIG. 7, if the stopper member 132 is raised and disposed at the highest position L2, then since the bottom portion of the stopper member 132 is separated from the bottom portion of the deformable member 145, the external shape of the deformable member 145 is able to deform elastically and freely in accordance with the change in the negative pressure.

Therefore, by means of the user rotating and adjusting the adjustment dial 100, the stopper member 132 can be moved upwards and downwards in the Z direction and registered in position and the volume by which the deformable member 145 can be deformed can thereby be altered, as a result of which the negative pressure (breast milk suctioning pressure) in the sealed space formed by the ventilation channel 23 of the milk expressing section, the ventilation channel 27, and the bottom section 52 of the deformable member 145 inside the case 110 can be adjusted finely.

As stated previously, the breast pump 20 according to the present embodiment is composed as stated above and the overall operation thereof is described below.

As shown in FIG. 2, a sealed space is formed when the user's breast M is abutted inside the milk expressing section 22. FIG. 2 shows a state before the motor 41 and the diaphragm 45 perform a suctioning operation, and FIG. 3 shows an example of a state where the motor 41 and the diaphragm 45 are performing a suctioning operation and the pressure adjustment means or structure 44 is adjusting the negative pressure inside the ventilation channels 23 and 27 of the milk expressing section.

The deformable member 145 shown in FIG. 2 occupies a large volume of the internal space of the case 110, which is a portion of the sealed space.

As shown in FIG. 3, when the motor 41 and the diaphragm 45 are driven to create a vacuum suction, the air pressure inside the deformable member 145 declines via the ventilation channel 43 and the opening 51 in the deformable member 145. Therefore, as shown in FIG. 3, due to the pressure differential with respect to the outside space, the bottom section 52 approaches the side of the opening 51 so as to press and squash the internal space of the deformable member 145, and therefore the deformable member 145 is deformed.

As shown in the change from the state in FIG. 2 to the state in FIG. 3, the bottom section 52 of the deformable member 145 displaces so as to approach the opening 51, thereby greatly decreasing the volume inside the deformable member 145, and therefore the air pressure inside the sealed space connected to the internal space (the sealed space formed by the ventilation channel 23 of the milk expressing section, the ventilation channel 27 and the bottom section 52 of the deformable member 145 inside the case 110) is greatly reduced. In other words, since the negative pressure increases inside the sealed space which is connected to the internal space, then breast milk is suctioned from the breast M and the breast milk thus expressed passes along the ventilation channel 23 and falls down into the small chamber 26. Moreover, in this case, the convex-shaped stimulating sections 14 of the deformable member 13 deform toward the breast side in accordance with the pressure differential, and the vicinity of the areola, or the like, is pressed and stimulated, whereby it is possible further to prompt the secretion of breast milk.

Next, when the negative pressure state inside the ventilation channel 43 is released due to the operation of the motor 41 and the diaphragm 45 shown in FIG. 3, the bottom section 52 of the deformable member 145 moves away from the opening 51 and descends, and the bottom section 52 is displaced so as to restore the form of the deformable member 145 again as shown in the change from the state in FIG. 3 to the state in FIG. 2. By this means, the deformable member 145 is able to increase volume inside the case 110, and therefore the air pressure inside the sealed space rises and the breast milk suctioning pressure decreases.

By repeating the negative pressure generating operation shown in FIG. 3 and the negative pressure generation release operation shown in FIG. 2, as described above, the action of the motor 41 and the diaphragm 45 which form the pressure changing means or structure is transmitted to the sealed space by the movement of the deformable member 145, and the negative pressure in the sealed space rises or falls, whereby a state close to the suckling action of a baby is achieved, and expressed breast milk can be collected in the bottle 47.

Since the deformable member 145 of the pressure transmitting section 30 is disposed so as to make close contact with the interior of the case 110, then the sealed space of the milk expressing section 22 and the pressure changing means or structure, such as the motor 41 and the diaphragm 45, are separated from each other in a completely liquid-tight and air-tight fashion. Therefore, any breast milk which has stagnated in the small chamber 26 or the like, or breast milk which has formed a mist, can be prevented effectively from entering inside the motor 41 and the diaphragm 45. Consequently, the pressure changing means or structure, such as the motor 41 and the diaphragm 45, and the like, never makes direct contact with the breast milk and therefore it is possible to prevent effectively the occurrence of corrosion or damage, or soiling and the occurrence of an unhygienic state.

When the negative pressure generating operation such as that shown in FIG. 2 and FIG. 3 is performed, then the user is able to change and finely adjust the negative pressure (suctioning pressure) inside the sealed space created by the ventilation channel 23 of the milk expressing section, the ventilation channel 27 and the bottom section 52 of the deformable member 145 in the case 110, in a desired linear fashion without the occurrence of a steep gradient, by rotating and operating the adjustment dial 100 of the pressure adjustment means or structure 44 shown in FIG. 5 and FIG. 6, as desired, in the W direction, with her finger.

For instance, in the state shown in FIG. 2 and FIG. 6, the stopper member 132 is disposed in the lowermost position L1, and the outer shape of the deformable member 145 is kept reliably at a position of the bottom section of the case 110 by means of the stopper member 132. Therefore, the stopper member 132 is not able to perform elastic deformation freely due to the change in the pressure of the deforming member 145, and the contraction of the deformable member 145 due to the suctioning pressure is restricted mechanically.

Therefore, if the user feels that the suction pressure is weak, then she rotates the adjustment dial 100 with her finger about the central axis CL with respect to the base section 130, whereby the rotating member 131 is turned about the central axis R with respect to base section 130, due to the rotation of the adjustment dial 100. Consequently, due to the intermeshing between the male screw section 140 of the stopper member 132 and the female screw section 139 of the rotating member 131, the stopper member 132 progressively rises upward in the Z1 direction as shown from the state in FIG. 2 to the state in FIG. 3, and from the state in FIG. 6 to the state in FIG. 7. The amount by which the stopper member 132 rises in the Z1 direction is proportional to the amount of rotation of the adjustment dial 100.

By this means, it is possible to adjust the height position of the stopper member 132 between the lowermost position L1 and the uppermost position L2, as shown in FIG. 3, whereby the bottom section of the stopper member 132 is separated from the bottom section 52 of the deformable member 145 in accordance with the position of the stopper member 132, and therefore the outer shape of the deformable member 145 is not constricted by the stopper member 132. Consequently, the outer shape of the deformable member 145 is able freely to deform elastically due to the change in the pressure, and the deformable member 145 is able to deform in accordance with the suctioning pressure. As a result of this, by rotating and adjusting the adjustment dial 100, the user is able to move the stopper member 132 upwards and downwards and determine the position thereof, thus making it possible to change and finely adjust, in a linear fashion, the pressure inside the sealed space which is created by the ventilation channel 23 of the milk expressing section, the ventilation channel 27 and the bottom section 52 of the deformable member 145 inside the case 110.

In this way, while expressing milk, the user is able to adjust and reduce the suctioning pressure easily, and also reliably, simply by operating and turning the adjustment dial 100. Moreover, the amount by which the stopper member 132 is raised in the Z1 direction changes in direct proportion to the amount of rotation of the adjustment dial 100, and consequently, it is possible to finely adjust and increase the suctioning pressure in a linear fashion.

Furthermore, the user is able to adjust and reduce the suctioning pressure easily, and also reliably, simply by operating and turning the adjustment dial 100 in the opposite direction. Moreover, the amount by which the stopper member 132 is lowered in the Z2 direction changes in direct proportion to the amount of rotation of the adjustment dial 100, and it is possible to finely adjust and reduce the suctioning pressure in a linear fashion.

Figure 9:
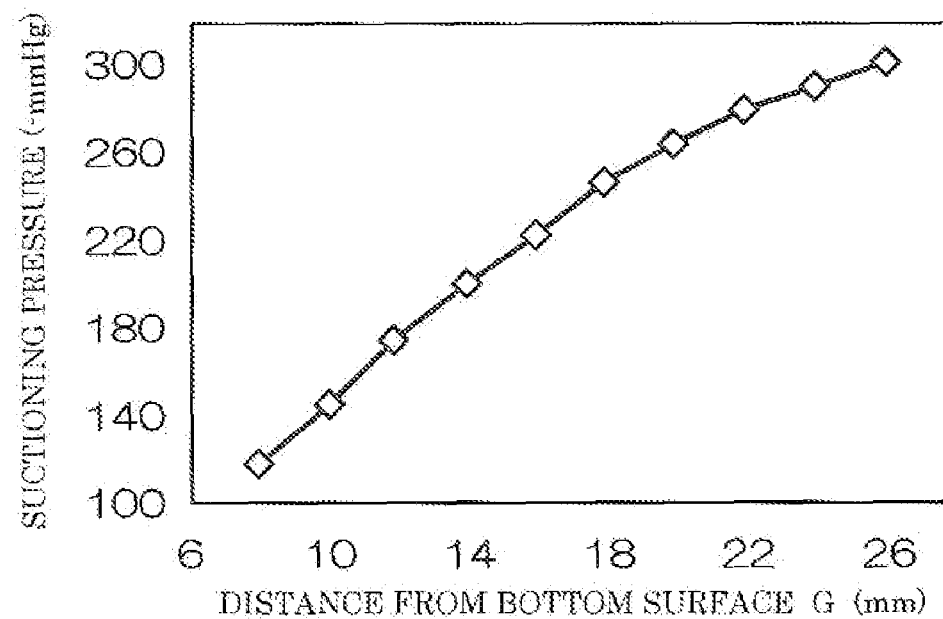
FIG. 9 shows the results of measuring examples of the relationship between the distance (mm) of separation of the bottom section of a stopper from the bottom internal face of a cup, and the suctioning pressure (mmHg), in other words, examples of pressure adjustment.
Figure 9:
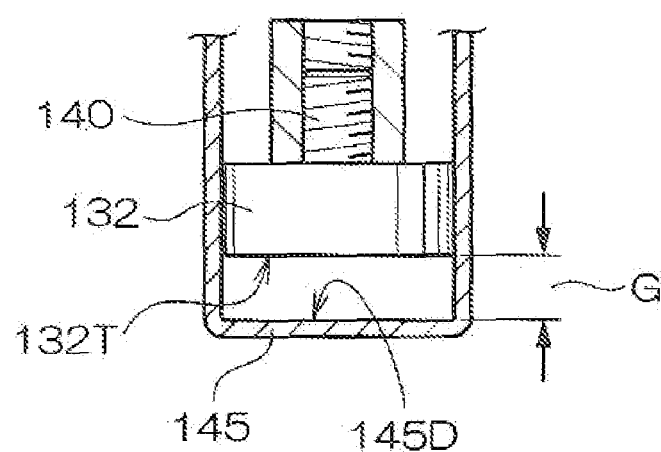

FIG. 9 is a diagram showing the results of measuring the relationship between the distance G (mm) of separation of the bottom section 132T of the stopper member 132 from the inner bottom surface 145D of the deformable member 145, and the suctioning pressure (-mmHg), in other words, examples of pressure adjustment of the deformable member 145.

FIG. 9 shows a case where the distance G and the suctioning pressure are substantially in direct proportion. The reason for this is that because, as stated previously, the gear 134 of the adjustment dial 100 intermeshes with the gear 135 of the rotating member 131 and moreover the male screw section 140 of the stopper member 132 intermeshes with the female screw section 139 of the rotating member 131, then when the user turns the adjustment dial 100 about the central axis CL with respect to the base section 130, the rotating member 131 also turns in a coupled fashion about the central axis R.

Therefore, due to the intermeshing between the male screw section 140 of the stopper member 132 and the female screw section 139 of the rotating member 131, the stopper member 132 progressively rises upward in the Z1 direction as shown from FIG. 2 to FIG. 3, and from FIG. 6 to FIG. 7. The amount by which the stopper member 132 rises in the Z1 direction is proportional to the amount of rotation of the adjustment dial 100. Furthermore, if the user operates and turns the adjustment dial 100 in the opposite direction about the central axis CL, then the stopper member 132 shown in FIG. 7 descends progressively in the Z2 direction, and the amount by which the stopper member 132 descends in this case is also directly proportional to the amount of rotation of the adjustment dial 100.

Figure 10:
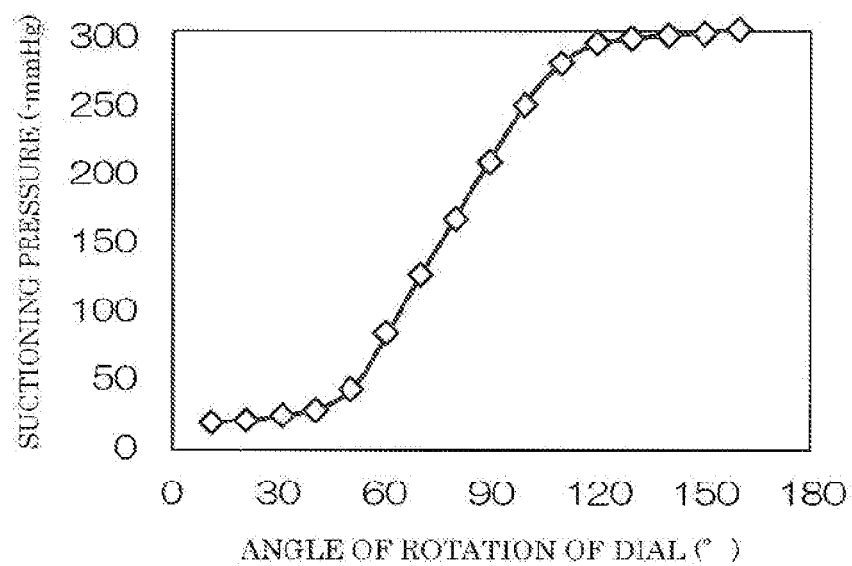
FIG. 10 is a diagram showing a relationship between the angle of rotation of the dial and suctioning pressure in a breast pump according to the related art.

Therefore, in contrast to the prior art example shown in FIG. 10, the user is able to change the deformable volume of the deformable member 145 in direct proportion to the amount of turning operation of the adjustment dial 100. More specifically, it is possible readily to adjust the suctioning pressure in a linear fashion without the occurrence of a steep gradient, and the user is able to perform an operation of raising or lowering the suctioning pressure, according to her own sensory perception.

By means of the user operating the adjustment dial 100, it is possible to adjust the negative pressure (suctioning pressure) in a linear fashion without the occurrence of a steep gradient, in accordance with the amount of operation, and it is possible readily to adjust the negative pressure even during the expression of milk. More specifically, by means of the user simply turning the adjustment dial 100, the stopper member 132 is caused to project inside the deformable member 145, and the negative pressure (suctioning pressure) can be adjusted in accordance with the amount of projection of stopper 145 in a linear fashion without the occurrence of a steep gradient, and therefore the reduction and increase of the negative pressure can be adjusted readily, even during the expression of milk.

Next, a further embodiment of the present disclosed subject matter will be described with reference to FIGS. 8A and 8B.

FIGS. 8A and 8B show pressure adjustment means or structure 44A according to a further embodiment of the present disclosed subject matter; FIG. 8A shows the internal state of the deformable member 145 where the stopper member 232, which is a rotating body, is superimposed over a wall portion 239 of the base portion 230.

The stopper member 232 has a substantially semicircular shape when viewed from above, and the wall portion 239 has a semicircular shape which inscribes the stopper member 232 when viewed from above.

FIG. 8B shows a state where the stopper member 232 is projecting out in the C direction about the central axis R, with respect to the wall portion 239 of the base section 230. The pressure adjustment means or structure 44A in FIG. 8A can be used instead of the pressure adjustment means or structure 44 shown in FIG. 2 and FIG. 3 and described previously.

As shown in FIG. 8A, the pressure adjustment means or structure 44A comprises a substantially circular base section 230, a rotating member 231, a stopper member 232, and an adjustment dial 100. The base section 230 has an attachment section 233 provided about the whole circumferential direction, and by fitting the attachment section 233 into the upper end portion 110A of the case 110 shown in FIG. 4, the base section 230 is fixed so as to seal off the upper end portion of the case 110. An adjustment dial 100 is installed rotatably about the central axis CL on the upper face of the base section 230. A gear 134 is formed about the whole of the outer circumference of the adjustment dial 100. The base section 230 comprises a tubular case portion 236 and a wall portion 239 having a quarter-tube shape, for example. The case portion 236 and the wall portion 239 are formed concentrically about the central axis R.

Figure 8:
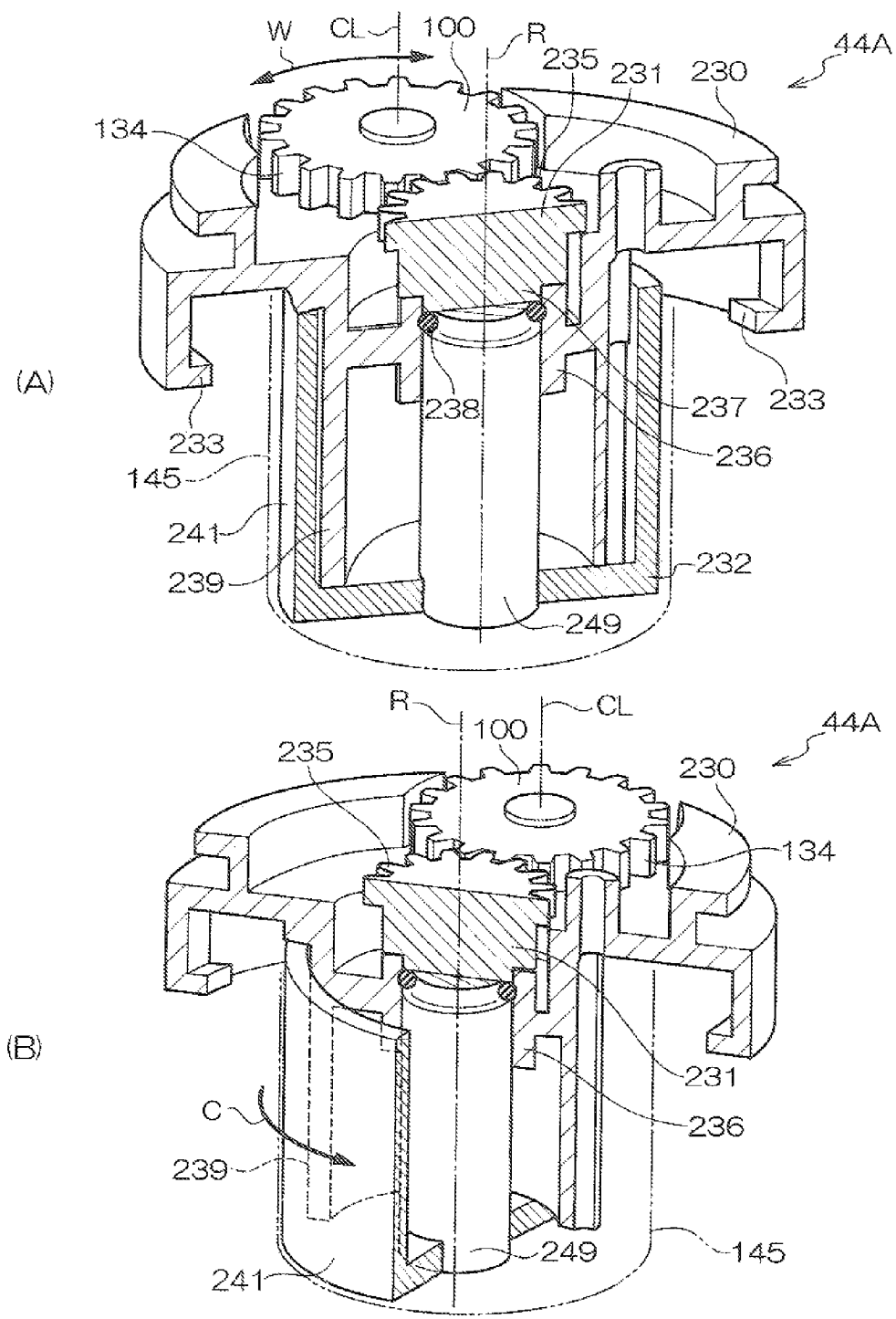
FIGS. 8A and 8B are perspective diagrams showing a further embodiment of a breast pump according to the presently disclosed subject matter.

The rotating member 231 in FIG. 8 is a columnar member, and a gear 235 is formed about the whole circumference of an upper position of the outer circumferential portion of the rotating member 231. This gear 235 intermeshes with a gear 134. A lower position 237 of the outer circumferential surface of the rotating member 231 is installed rotatably about the central axis R on the case section 236 of the base section 230. The lower position 237 of the rotating member 231 is tapped and joined to the upper end portion of the columnar section 249 of the stopper member 232, so as to move in unison with same. An O ring 238 is provided in order to create a hermetic seal on the lower position 237 of the rotating member 231, the case section 236 and the upper end central portion 249 of the stopper member 232. The central axis CL and the central axis R are mutually parallel and lie in the vertical direction.

There are no particular restrictions on the material used for the stopper member 232 shown in FIGS. 8A and 8B, and good reproducibility of pressure adjustment is achieved if a hard member made of ABS, polycarbonate, polypropylene, or the like, is used.

The stopper member 232 has a columnar section 249 and a partial tubular section 241 having a tube shape. The partial tubular section 241 of the stopper member 232 is disposed to the outer side of the wall portion 239 of the base section 230, and the partial tubular section 241 and the wall portion 239 are formed coaxially about the central axis R. The partial tubular section 241 is disposed to the inner side of the deformable member 145 shown in FIG. 2.

Accordingly, by means of the user appropriately rotating the adjustment dial 100 in the W direction with her finger, the adjustment dial 100 is able to cause the rotating member 231 to turn in the direction opposite to the direction of rotation of the adjustment dial 100. Therefore, due to the rotation of the rotating member 231, the partial tubular section 241 of the stopper member 232 can be made to project out in the C direction so as to adopt the state shown in FIG. 8B, from the state shown in FIG. 8A.

The stopper member 232 is positioned inside the deformable member 145 shown in FIG. 2 and FIG. 4. In the state shown in FIG. 8A, the stopper member 232 is in a state whereby the outer shape of the deformable member 145 can be deformed elastically by approximately one half of the volume thereof, due to the suctioning pressure. However, in the state shown in FIG. 8B, by causing the partial tubular section 241 of the stopper member 232 to project out in the C direction, the volume by which the deformable member 145 can deform elastically is reduced due to the partial tube of the stopper member 232 increasing the amount of inscription on the inside of the deformable member 145, by approximately ¼ of the circumference, for example. In other words, the deformation is restricted.

More specifically, since the partial tubular section 241 of the stopper member 232 is caused to project out from the wall portion 239 by a desired length in the C direction as indicated in the change from the state shown in FIG. 8A to the state shown in FIG. 8B, then it is possible to inhibit the deformation of the outer shape of the deformable member 145 due to the suctioning pressure, by means of the partial tubular section 241 which has been made to project out from the wall portion 239 abutting against the inner bottom surface of the deformable member 145.

In this way, the pressure adjustment means or structure 44A shown in FIGS. 8A and 8B comprises a base section 230 having a wall portion 239 which upstands inside the deformable member 145, an adjustment dial 100 provided on the base section 230, which can be turned by the user, and a partial tubular section 241 which adjusts the amount of deformation of the deformable member 145 by rotating from a state overlapping with the wall portion 239 of the base section 230, and being made to project from the wall portion 239 toward the interior of the deformable member 145, due to the rotation of the adjustment dial 100. By this means, in contrast to the prior art examples shown in FIG. 10, the user is able readily to adjust the suctioning pressure in a linear fashion without the occurrence of a steep gradient, in direct proportion to the amount of turning operation of the adjustment dial 100, and hence the user is able to perform the operation of raising or lowering the suctioning pressure, according to her own sensory perception. By means of the operation performed by the user, it is possible to adjust the negative pressure (suctioning pressure) in accordance with the amount of operation in a linear fashion without the occurrence of a steep gradient, and hence it is possible readily to adjust the negative pressure even during the expression of milk. In other words, simply by means of the user turning the adjustment dial, the partial tubular section is made to project inside the deformable member from the wall portion, and the user is able to adjust the negative pressure (suctioning pressure) in accordance with the amount of rotation of the partial tubular section in a linear fashion without the occurrence of a steep gradient, thus making it possible to readily adjust the negative pressure even during the expression of milk.

It should be noted that the present disclosed subject matter is not limited to the embodiments described above.

For example, it is also possible to provide a lever instead of the adjustment dial 100 shown in FIG. 6 and to turn the rotating member 131 by operating and turning this lever. The position in which the pressure transmitting section 30 is disposed can be altered as desired and is not limited to that shown in the drawings. A weak portion can be provided in the wall face of the deformable section by either reducing the material thickness in a partial fashion, or by disposing a flexible material.

Furthermore, the individual compositional elements of the embodiments and modification examples described may be omitted according to requirements, and combined with other compositions which are not described.

While there has been described what are at present considered to be exemplary embodiments of the invention, it will be understood that various modifications may be made thereto, and it is intended that the appended claims cover such modifications as fall within the true spirit and scope of the invention. All conventional art references described above are herein incorporated in their entirety by reference.

What is claimed is:

1. A breast pump having a substantially conical milk expressing section configured to abut against a user's breast, and a breast pump main body which includes the milk expressing section and is attachable to and detachable from a bottle so as to communicate with the bottle, comprising:
a pressure changing structure, connected to the milk expressing section, for alternately generating a negative pressure state and at least an atmospheric pressure state as a pressure higher than the negative pressure state;
a deformable member configured to liquid-tightly separate a sealed space formed by abutment of the milk expressing section against the user's breast and a space connected to the sealed space, from the pressure changing structure, and which is capable of being deformed by transmission of the pressure that is changed by the pressure changing structure in order to adjust the pressure state of the milk expressing section; and
a pressure adjustment structure for adjusting the negative pressure state by changing an amount of deformation of the deformable member while not adjusting a leakage volume of air.

2. The breast pump according to claim 1, wherein the sealed space includes a first space portion defined at least in part by the conical milk expressing section and a second space portion defined at least in part by the deformable member which is connected to the pressure changing structure, the first space portion being separate from the second space portion but in fluid communication therewith.

3. The breast pump according to claim 1, wherein the pressure adjustment structure includes,
a base section,
an adjustment dial provided on the base section and configured to be rotated by the user, and
a stopper provided inside the deformable member and configured to adjust the amount of deformation of the deformable member by moving with respect to the base section due to rotation of the adjustment dial.

4. The breast pump according to claim 1, wherein the pressure adjustment structure includes,
a base section having a wall portion which upstands inside the deformable member,
an adjustment dial provided on the base section and configured to be rotated by the user, and
a partial tubular section provided inside the deformable member and configured to adjust the amount of deformation of the deformable member by projecting inside the deformable member from the wall portion by rotating from a state of overlapping with the wall portion of the base section, due to rotation of the adjustment dial.

5. The breast pump according to claim 3, wherein the pressure adjustment structure includes,
a base section having a wall portion which upstands inside the deformable member,
an adjustment dial provided on the base section and configured to be rotated by the user, and
a partial tubular section provided inside the deformable member and configured to adjust the amount of deformation of the deformable member by projecting inside the deformable member from the wall portion by rotating from a state of overlapping with the wall portion of the base section, due to rotation of the adjustment dial.

6. A breast pump having a substantially conical milk expressing section configured to abut against a user's breast, and a breast pump main body which includes the milk expressing section and is attachable to and detachable from a bottle so as to communicate with the bottle, comprising:
pressure changing structure, connected to the milk expressing section, configured to alternately generate a negative pressure state and at least an atmospheric pressure state as a pressure higher than the negative pressure state;
a deformable member configured to liquid-tightly separate a sealed space formed by abutment of the milk expressing section against the user's breast and a space connected to the sealed space, from the pressure changing structure, and which is configured to deform in order to adjust the negative pressure state of the milk expressing section by transmission of the pressure that is changed by the pressure changing structure; and
in the case of increase or decrease of a suctioning pressure of the pressure changing structure pressure adjustment structure configured to adjust the negative pressure state by changing an amount of deformation of the deformable member.

7. The breast pump according to claim 6, wherein the pressure adjustment structure includes,
 a base section,
 an adjustment dial provided on the base section and configured to be rotated by the user, and
 a stopper provided inside the deformable member and configured to adjust the amount of deformation of the deformable member by moving with respect to the base section due to rotation of the adjustment dial.

8. The breast pump according to claim 6, wherein the pressure adjustment structure includes,
 a base section having a wall portion which upstands inside the deformable member,
 an adjustment dial provided on the base section and configured to be rotated by the user, and
 a partial tubular section provided inside the deformable member and configured to adjust the amount of deformation of the deformable member by projecting inside the deformable member from the wall portion by rotating from a state of overlapping with the wall portion of the base section, due to rotation of the adjustment dial.

9. The breast pump according to claim 7, wherein the pressure adjustment structure includes,
 a base section having a wall portion which upstands inside the deformable member,
 an adjustment dial provided on the base section and configured to be rotated by the user, and
 a partial tubular section provided inside the deformable member and configured to adjust the amount of deformation of the deformable member by projecting inside the deformable member from the wall portion by rotating from a state of overlapping with the wall portion of the base section, due to rotation of the adjustment dial.

* * * * *